United States Patent [19]

Grisar et al.

[11] 4,200,755

[45] Apr. 29, 1980

[54] 2-HYDROXY-5-[1-HYDROXY-2-[4-(2-OXO-1-BENZIMIDAZOLINYL)PIPERIDINO]ETHYL]BENZOIC ACID DERIVATIVES

[75] Inventors: J. Martin Grisar; George P. Claxton, both of Cincinnati, Ohio

[73] Assignee: Richardson-Merrell Inc., Wilton, Conn.

[21] Appl. No.: 36,245

[22] Filed: May 4, 1979

[51] Int. Cl.$^2$ ............................................. C07D 401/04
[52] U.S. Cl. ................................. 546/199; 546/271; 424/263; 424/267
[58] Field of Search ............................... 546/199, 271

[56] References Cited

U.S. PATENT DOCUMENTS

| | | | |
|---|---|---|---|
| 3,196,157 | 7/1965 | Janssen | 546/199 |
| 3,318,900 | 5/1967 | Janssen | 546/199 |
| 3,818,017 | 6/1974 | Janssen et al. | 546/271 |
| 3,894,030 | 7/1975 | Janssen et al. | 546/199 |
| 3,929,801 | 12/1975 | Janssen et al. | 546/199 |
| 4,080,328 | 3/1978 | Maruyama et al. | 546/199 |

*Primary Examiner*—Alan L. Rotman
*Assistant Examiner*—Natalia Harkaway
*Attorney, Agent, or Firm*—William J. Stein; Eugene O. Retter; George W. Rauchfuss, Jr.

[57] ABSTRACT

Derivatives of 2-hydroxy-5-[1-hydroxy-2-[4-(2-oxo-1-benzimidazolinyl)piperidino]ethyl]benzoic acid are prepared which are useful for their blocking action on α and β-adrenergic receptors. In addition, these compounds are useful for their spasmolytic and anti-hypertensive activity.

6 Claims, No Drawings

2-HYDROXY-5-[1-HYDROXY-2-[4-(2-OXO-1-BEN-ZIMIDAZOLINYL)PIPERIDINO]ETHYL]BENZOIC ACID DERIVATIVES

DESCRIPTION

Field of the Invention

This invention relates to 2-hydroxy-5-[1-hydroxy-2-[4-(2-oxo-1-benzimidazolinyl)piperidino]ethyl] derivatives of benzoic acid and their preparation.

SUMMARY OF THE INVENTION

This invention relates to novel derivatives of 2-hydroxy-5-[1-hydroxy-2-[4-(2-oxo-1-benzimidazolinyl)-piperidino]ethyl]benzoic acid. More particularly, this invention relates to certain 2-hydroxy, 2-methoxy and 2-ethoxy derivatives of 5-[1-hydroxy-2-[4-(2-oxo-1-benzimidazolinyl)piperidino]ethyl]benzoic acid or benzamide. Still more particularly, this invention relates to derivatives of 2-hydroxy-5-[1-hydroxy-2-[4-(2-oxo-1-benzimidazolinyl)piperidino]ethyl]benzoic acid having the general formula

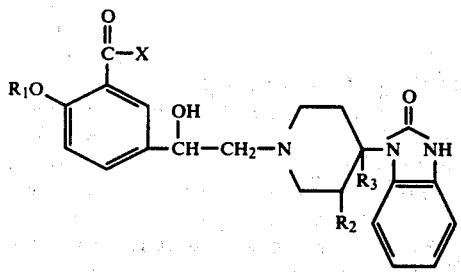

(I)

wherein X is selected from the group consisting of hydroxy, methoxy, ethoxy, amino, dimethylamino and alkylamino in which the alkyl group has from 1 to 12 carbon atoms; $R_1$ is hydrogen, methyl or ethyl; $R_2$ and $R_3$ are hydrogen or when taken together form a double bond; and the pharmaceutically acceptable acid addition salts thereof.

This invention further discloses a method whereby these derivatives may be conveniently prepared and in good yield.

DETAILED DESCRIPTION OF THE INVENTION

As seen in general formula (I) above, all of the compounds of this invention contain a 1-hydroxy-2-[4-(2-oxo-1-benzimidazolinyl)piperidino]ethyl] moiety attached to the 5-position of the phenyl ring. The remaining two variable groups attached to the phenyl ring, as represented by the symbol X and $R_1$, include among other substituents the carboxyl and hydroxyl functions, respectively. Thus, for purposes of uniformity of nomenclature, all of the compounds described herein are designated as 2-hydroxy-5-[1-hydroxy-2-[4-(2-oxo-1-benzimidazolinyl)piperidino]ethyl]benzoic acid derivatives.

In addition to the various derivatives of benzoic acid described herein, the corresponding methyl and ethyl esters, as well as certain amides, are also contemplated as being within the scope of this invention. Thus, where the symbol X represents the methoxy and ethoxy groups, the methyl and ethyl esters of 2-hydroxy-5-[1-hydroxy-2-[4-(2-oxo-1-benzimidazolinyl)piperidino]ethyl]benzoic acid are contemplated.

Where the symbol X represents amino, dimethylamino and alkylamino the various substituted and unsubstituted benzamides are delineated. In the case of the N-alkyl-amino group, the amide nitrogen atom is substituted by an alkyl group having from 1 to 12 carbon atoms. Illustrative of the N-alkyl groups are methyl, ethyl, propyl, butyl, amyl, hexyl, heptyl, octyl, nonyl, decyl, undecyl and dodecyl. Those N-lower alkyl groups having from 1 to 4 carbon atoms delineate the preferred N-substituted benzamides. Additionally, the various branched and positional isomers are included within the scope of this invention as long as the alkyl group is univalent and does not exceed a total of 12 carbon atoms.

The symbol $R_1$ is represented by hydrogen, or the methyl and ethyl groups. Where $R_1$ is hydrogen and X is hydroxy, the compounds can be designated as 5-[1-hydroxy-2-[4-(2-oxo-1-benzimidazolinyl)piperidino]ethyl]derivatives of salicylic acid. However, for uniformity of nomenclature, these compounds will be termed as derivatives of 2-hydroxy-5-[1-hydroxy-2-[4-(2-oxo-1-benzimidazolinyl)piperidino]ethyl]benzoic acid.

As can be further seen in formula (I) above, the 4-position of the piperidine ring is substituted with a mandatory 2-oxo-1-benzimidazolinyl moiety. In addition, the piperidine ring can be unsaturated at the 3,4-positions. This unsaturation is indicated by the symbols $R_2$ and $R_3$ taken together to form a double bond. Compounds of this type are termed as 2-hydroxy-5-[1-hydroxy-2-[4-(2-oxo-1-benzimidazolinyl)-1,2,3,6-tetrahydro-1-pyridyl]ethyl]benzoic acid.

When the symbol X represents the amino, dimethylamino and alkylamino group in which the alkyl group has from 1 to 12 carbon atoms, and the symbols $R_1$, $R_2$ and $R_3$ are all hydrogen, a preferred class of benzamides is delineated within the broad scope of this invention.

A further preferred group of compounds within the scope of this invention is represented by the methyl and ethyl esters of benzoic acid. Thus, where the symbol X represents methoxy and ethoxy and the symbols $R_1$, $R_2$ and $R_3$ are hydrogen, a preferred sub-group of compounds is delineated.

The expression pharmaceutically acceptable acid addition salts encompasses any non-toxic organic or inorganic acid addition salts of the base compounds represented by formula (I). Illustrative inorganic acids which form suitable salts include hydrochloric, hydrobromic, sulfuric and phosphoric acid as well as acid metal salts such as sodium, monohydrogen ortho-phosphate and potassium hydrogen sulfate. Illustrative organic acids which form suitable salts include the mono-, di- and tri-carboxylic acids, for example, acetic, fumaric, malic, tartaric, citric, ascorbic, maleic, hydroxymaleic, benzoic, hydroxybenzoic, phenyl-acetic, cinnamic, salicylic, 2-phenoxybenzoic and sulfonic acids such as methane sulfonic acid, 2-hydroxyethane sulfonic acid, and benzenesulfonic acid. The salts that are formed can exist in either a hydrated or a substantially anhydrous form.

Illustrative specific free base compounds encompassed by formula (I) above include:
2-hydroxy-5-[1-hydroxy-2-[4-(2-oxo-1-benzimidazolinyl)piperidino]ethyl]benzoic acid,
2-ethoxy-5-[1-hydroxy-2-[4-(2-oxo-1-benzimidazolinyl)-piperidino]ethyl]benzoic acid,
5-[1-hydroxy-2-[4-(2-oxo-1-benzimidazolinyl)-piperidino]ethyl]-2-methoxybenzoic acid, 2-hydroxy-5-[1-hydroxy-2-[4-(2-oxo-1-benzimidazolinyl)-1,2,3,6-tetrahydro-1-pyridyl]ethyl]benzoic acid, methyl 2-hydroxy-5-[1-hydroxy-2-[4-(2-oxo-1-benzimidazolinyl)piperidino]ethyl]benzoate, ethyl 2-ethoxy-5-[1-hydroxy-2-[4-(2-oxo-1-benzimidazolinyl)piperidino]ethyl]benzoate, methyl 5-[1-hydroxy-2-[4-(2-oxo-1-benzimidazolinyl)-piperidino]ethyl]-2-methoxybenzoate, ethyl 2-hydroxy-5-[1-hydroxy-2-[4-(2-oxo-1-benzimidazolinyl)-1,2,3,6-tetrahydro-1-pyridyl]ethyl]benzoate, 2-hydroxy-5-[1-hydroxy-2-[4-(2-oxo-1-benzimidazolinyl)piperidino]ethyl]benzamide, 5-[1-hydroxy-2-[4-(2-oxo-1-benzimidazolinyl)-piperidino]ethyl]-2-methoxybenzamide, 2-ethoxy-5-[1-hydroxy-2-[4-(2-oxo-1-benzimidazolinyl)-piperidino]ethyl]-1,2,3,6-tetrahydro-1-pyridyl]ethyl]benzoate, 2-hydroxy-5-[1-hydroxy-2-[4-(2-oxo-1-benzimidazolinyl)piperidino]ethyl]-N,N-dimethylbenzamide, 2-ethoxy-5-[1-hydroxy-2-[4-(2-oxo-1-benzimidazolinyl)-piperidino]ethyl]-N-ethylbenzamide, 5-[1-hydroxy-2-[4-(2-oxo-1-benzimidazolinyl)-piperidino]ethyl]-2-methoxy-N-butylbenzamide, 2-hydroxy-5-[1-hydroxy-2-[4-(2-oxo-1-benzimidazolinyl)-1,2,3,6-tetrahydro-1-pyridyl]ethyl]-N,N-dimethylbenzamide, 2-ethoxy-5-[1-hydroxy-2-[4-(2-oxo-1-benzimidazolinyl)-piperidino]ethyl]-N-heptylbenzamide, 5-[1-hydroxy-2-[4-(2-oxo-1-benzimidazolinyl)-piperidino]ethyl]-2-methoxy-N-decylbenzamide, and 2-hydroxy-5-[1-hydroxy-2-[4-(2-oxo-1-benzimidazolinyl)-1,2,3,6-tetrahydro-1-pyridyl]ethyl]-N-dodecylbenzamide.

The 2-hydroxy-5-[1-hydroxy-2-[4-(2-oxo-1-benzimidazolinyl)piperidino]ethyl]benzoic acid derivatives of formula (I) are readily prepared by condensing a derivative of 2-hydroxy-5-(2-bromoacetyl)benzoic acid (II) with a 4-(2-oxo-1-benzimidazolinyl)piperidine (III). The resulting 2-hydroxy-5-[4-(2-oxo-1-benzimidazolinyl)piperidinoacetyl]benzoic acid derivative (IV) is subsequently reduced to the desired derivative of 2-hydroxy-5-[1-hydroxy-2-[4-(2-oxo-1-benzimidazolinyl)piperidino]ethyl]benzoic acid (I). This process may be schematically illustrated as follows:

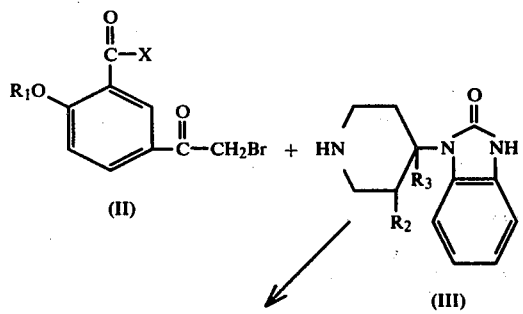

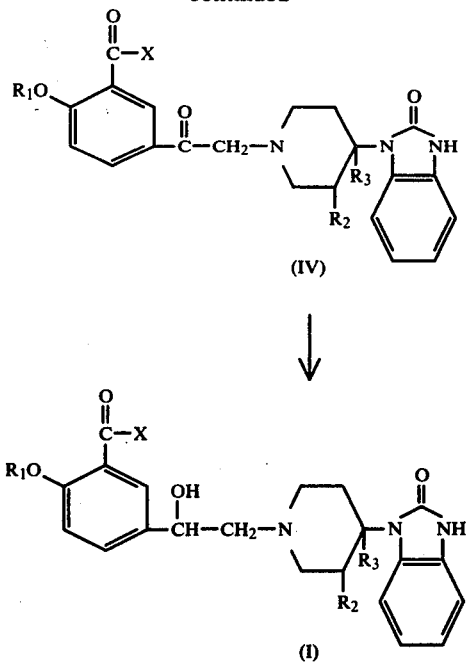

The 2-hydroxy-5-(2-bromoacetyl)benzoic acid derivatives (II) are readily obtained via the bromination of the corresponding known 2-hydroxy-5-acetyl-benzoic acid derivatives. Bromination is conducted in an inert solvent such as chloroform or tetrahydrofuran by the addition of a brominating agent such as bromine, cupric bromide, pyrrolidone-2 hydrotribromide and phenyltrimethylammonium perbromide. Where the symbol X is the methoxy or ethoxy groups, the use of bromine is most convenient.

The condensation to the 2-hydroxy-5-[4-(2-oxo-1-benzylimidazolinyl)piperidinoacetyl]benzoic acid derivatives (IV) is conducted in a suitable anhydrous solvent such as diethyl ether, tetrahydrofuran or dimethylformamide. The resulting hydrobromic acid that is released during the reaction is captured by the 2-hydroxy-5-[4-(2-oxo-1-benzylimidazolinyl)piperidino-acetyl]benzoic acid derivative that forms. More conveniently, an equivalent of triethylamine or a base that is stronger in basicity than the desired 5-[4-(2-oxo-1-benzimidazolinyl)piperidinoacetyl]benzoic acid derivative (IV) can be added to form a hydrobromide salt which can be readily separated from the reaction mixture.

The condensation reaction proceeds at a reasonable rate at room temperature and is slightly exothermic. Control of the reaction time and temperature is important inasmuch as the carbonyl groups present in the 2-hydroxy-5-(2-bromoacetyl)benzoic acid derivatives (II) and the 2-hydroxy-5-[4-(2-oxo-1-benzimidazolinyl)-piperidinoacetyl]benzoic acid derivatives that form (IV) can also undergo reactions with the 4-(2-oxo-1-benzimidazolinyl)piperidine, resulting in undesirable side products. The condensation can be conducted at a temperature range of from about 0° to 50° C. and for a period of time ranging from 1 hour to 3 days. Preferably, a temperature of from 20°–30° C. and a reaction time of from 2 to 16 hours is employed. The slow addition of the 2-hydroxy-5-(2-bromoacetyl)benzoic acid derivatives to the 4-(2-oxo-1-benzimidazolinyl)piperidine is also found to be advantageous.

Reduction of the 2-hydroxy-5-[4-(2-oxo-1-benzimidazolinyl)piperidinoacetyl]benzoic acid derivatives (IV) to the corresponding alcohols of the present invention (I) can be achieved using a variety of reagents. Where the symbol X represents the methoxy and ethoxy groups, it is important to use a selective reducing agent that will reduce only the 5-(substituted)acetyl ketone and not the ester functions or the 2-oxo-1-benzimidazolinyl ketone function as well. The reduction can be achieved by hydrogenation in the presence of a noble metal catalyst such as platinum, palladium or rhodium on charcoal. Preferably, a palladium on charcoal catalyst is employed.

Alternatively, a suitable metal hydride reagent may be employed. The choice of the particular hydride reagent to be employed is dependent upon the nature of the symbol X. Thus, where X results in an ester or amide function, the reagent must be one that reduces only the desired 5-(substituted)acetyl ketone and not the carbonyl ester or amide function. Where X represents the methoxy or ethoxy group, sodium borohydride in a solvent such as methanol at a temperature of from 0° to 20° C. is preferably employed. In the event that a stereoselective reduction is desired, the use of certain highly hindered lithium or potassium trialkylborohydride reagents may be favorably employed, as for example lithium B-isopino-campheyl-9-borabicyclo[3.3.1]nonyl hydride, cf., Krishnamurthy et al., J. Org. Chem., 42, 2534 (1977).

In the case where the symbol X represents a carboxyl or an amide function, it may be desirable to first prepare the corresponding methyl or ethyl ester of the 2-hydroxy-5-[1-hydroxy-2-[4-(2-oxo-1-benzimidazolinyl)-piperidino]ethyl]benzoic acid derivative desired and subsequently hydrolyze it to the corresponding free acid or convert it to the particular amide desired. Hydrolysis of the methyl or ethyl esters of (I) to the corresponding free acids can be achieved using either aqueous acid or alkali in accordance with standard procedures well known to those skilled in the art.

The conversion of the methyl or ethyl esters (I) to the corresponding amides, N-substituted or N,N-dimethylamide is conducted using an excess of ammonia or the appropriate amine in an alcoholic solvent. Preferably methanol is employed. If a gaseous amine is employed, such as ammonia or methylamine, the reaction temperature should be maintained at 25° C. or lower, unless the reaction is conducted in a suitable closed pressurized vessel. The amide conversion reaction can be facilitated by the use of a catalyst such as sodium methoxide, sodium amide or dimethylaluminumamide (A. Basha et al., Tetrahedron Letters, 1977, pp. 4171-7). In most cases freshly prepared sodium methoxide provides satisfactory results.

The compounds of formula (I) possess $\alpha$ and $\beta$-adrenergic receptor blocking activity and are useful in the treatment or prophylaxis of cardiovascular disorders, as for example arrhythmias, coronary heart disease, angina pectoris and hypertension in mammals. In addition, these compounds possess useful spasmolytic activity in mammals. The term mammals is intended to include inter alia such mammals as mice, rats, guinea pigs, rabbits, ferrets, dogs, cats, cows, horses and primates including man.

The 2-hydroxy-5-[1-hydroxy-2-[4-(2-oxo-1-benzimidazolinyl)piperidino]ethyl]benzoic acid derivatives can be administered as their pharmaceutical salts in combination with a pharmaceutical carrier using conventional dosage unit forms. Suitable dosage unit forms include oral preparations such as tablets, capsules, powders, granules, oral solutions and suspensions, sublingual and intrabuccal preparations, as well as parenteral dosage unit forms useful for subcutaneous intramuscular or intravenous administration.

The amount of the active ingredient to be administered can vary widely according to the particular dosage unit employed, the period of treatment, the age and sex of the patient treated and the nature and extent of the disorder treated. The total amount of active ingredient to be administered will generally range from about 1 mg/kg to 100 mg/kg and preferably from 3 mg/kg to 25 mg/kg. A unit dosage may contain from 25 to 500 mg. of active ingredient, preferably from 100 to 250 mg of active ingredient, and can be taken one or more times per day.

The preferred route of administration is via oral administration. Illustrative dosage levels of the active ingredient for oral administration range from 1 to 100 mg/kg of body weight. Preferably from 3 to 25 mg/kg of the active ingredient are orally administered in humans during a 24 hour period. In those instances where the drug is administered by the parenteral route, corresponding lower dosages are usually employed.

Formulations for oral use may be presented as hard or soft shelled gelatin capsules containing only the active ingredient, but generally blended with conventional pharmaceutical carriers or excipients such as gelatin, various starches, lactose, calcium phosphate, or powdered sugar. The term pharmaceutical carrier is intended to include lubricants employed to improve the flow of tablet granulations and to prevent the adhesion of tablet material to the surfaces of tablet dies and punches. Suitable lubricants include, for example, talc, stearic acid, calcium stearate, magnesium stearate and zinc stearate. Also included in the definition of a pharmaceutical carrier as used herein are disintegrating agents added to assist the break up and dissolution of tablets following administration, dyes and coloring agents, and flavoring agents to enhance the aesthetic qualities of the tablets and make them more acceptable to the patient.

Suitable liquid excipients for the preparation of liquid dosage unit forms include water and alcohols such as ethanol, benzyl alcohol and the polyethylene alcohols, either with or without the addition of a surfactant. In general, the preferred liquid excipients include water, saline solution, dextrose and glycol solutions, as for example an aqueous propylene glycol or an aqueous solution of polyethylene glycol. Liquid preparations to be used as sterile injectable solutions will ordinarily contain from about 0.5 to about 25% by weight, of the active ingredient in solution. In certain topical and parenteral preparations, various oils are utilized as carriers or excipients. Illustrative of such oils are mineral oils, glyceride oils such as lard oil, cod liver oil, peanut oil, sesame oil, corn oil, and soybean oil. Where a compound is insoluble in the particular vehicle chosen, suspending agents may be added as well as agents to control viscosity of the solution, as for example, magnesium aluminum silicate or carboxymethyl-cellulose. In addition to these excipients, buffers, preservatives and emulsifying agents may also be suitably employed.

The proportion of the active ingredient employed in parenteral dosage unit forms ranges from about 0.05 to about 20% by weight, preferably from about 0.1 to about 10% by weight of the total liquid composition, the remaining component or components comprising any of the various pharmaceutical excipients previously disclosed. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above-identified HLB, or a mixture of two or more components having the desired HLB. Illustrative of surfactants used in parenteral formulations are the class of polyoxyethylene sorbitan fatty acid esters as for example, sorbitan monooleate and the high molecular weight adducts of ethylene oxide with a hydrophobic base, formed by the condensation of propylene oxide with propylene glycol.

The invention herein described is more particularly illustrated in conjunction with the following specific Examples, but not necessarily limited thereto.

EXAMPLE 1

Methyl 2-hydroxy-5-[1-hydroxy-2-[4-(2-oxo-1-benzimidazolinyl)piperidino]ethyl]benzoate Hydrochloride A solution of 12.57 g (0.046 mol) of methyl 5-(2-bromoacetyl)-2-hydroxybenzoate dissolved in 60 ml of dry dimethylformamide is added via dropwise addition over a period of 60 minutes to a solution of 10.0 g (0.046 mol) of 4-(2-oxo-1-benzimidazolinyl)piperidine and 5.12 g (0.0506 mol) of triethylamine dissolved in 90 ml of dimethylformamide at 25° C. The reaction mixture is stirred for a period of 60 minutes at 25° C. and the triethylamine hydrobromide which precipitates is removed via filtration. The filtrate is poured into one liter of water and the product is extracted into methylene chloride. The combined extracts are washed with water, dried over sodium sulfate, and evaporated in vacuo leaving a residue (17.0 g) to which methanol and one equivalent of methanolic hydrogen chloride is added. The methyl 2-hydroxy-5-[4-(2-oxo-1-benzimidazolinyl)-piperidinoacetyl]benzoate which crystallizes (14.6 g) has a m.pt. of 229°-32° C. (dec.).

The methyl 2-hydroxy-5-[4-(2-oxo-1-benzimidazolinyl)piperidinoacetyl]benzoate is dissolved in one liter of methanol and cooled in an ice-methanol bath. Sodium borohydride (7.44 g) is added in portions over a period of 25 minutes. The mixture is stirred for approximately 30 minutes and poured onto one liter of ice-water. The mixture is acidified with 500 ml of a 10% acetic acid solution made basic by the addition of sodium bicarbonate and extracted with methylene chloride. The combined extracts are washed with water, dried over MgSO$_4$ which is removed by filtration, and the filtrate evaporated in vacuo leaving a residue of 11.3 g, having a m.pt. of 211°-13° C. (dec.). The residue is dissolved in one equivalent of methanolic hydrogen chloride and precipitated from solution with diethyl ether. Recrystallization of the precipitate from methanol yields methyl 2-hydroxy-5-[1-hydroxy-2-[4-(2-oxo-1-benzimidazolinyl)piperidino]ethyl]benzoate hydrochloride having a m.pt. of 229°-30° C. (dec.).

Following essentially the same procedure but substituting 4-(2-oxo-1-benzimidazolinyl)-1,2,3,6-tetrahydro-1-pyridine for the 4-(2-oxo-1-benzimidazolinyl)piperidine above results in the preparation of methyl 2-hydroxy-5-[1-hydroxy-2-[4-(2-oxo-1-benzimidazolinyl)-1,2,3,6-tetrahydro-1-pyridyl]ethyl]benzoate hydrochloride.

Following essentially the same procedure as above but substituting methyl 5-(2-bromoacetyl)-2-methoxybenzoate for the 5-(2-bromoacetyl)-2-hydroxybenzoate results in the formation of methyl 5-[1-hydroxy-2-[4-(2-oxo-1-benzimidazolinyl)piperidino]ethyl]-2-methoxybenzoate hydrochloride.

EXAMPLE 2

2-Hydroxy-5-[1-hydroxy-2-[4-(2-oxo-1-benzimidazolinyl)piperidino]ethyl]benzamide hydrochloride The compound methyl 2-hydroxy-5-[1-hydroxy-2-[4-(2-oxo-1-benzimidazolinyl)piperidino]ethyl]benzoate hydrochloride is converted to its free base by treatment with sodium bicarbonate solution and extraction into methylene chloride. The combined extracts are evaporated in vacuo and the residue dissolved in approximately 900 ml of anhydrous methanol to which a small piece (about 100 mg) of metallic sodium has been added. The mixture is cooled in an ice-methanol bath and saturated with gaseous ammonia. The reaction mixture is stirred at 25° C. until all of the ester is converted to the amide, as indicated by thin layer chromatography. Additional sodium methoxide catalyst and ammonia may have to be added. The reaction mixture, which becomes homogeneous, is evaporated to dryness in vacuo. Ethereal HCl is added to the residue and the product which crystallizes is recrystallized from an isopropanol-water mixture to yield 6.2 g of 2-hydroxy-5-[1-hydroxy-2-[4-(2-oxo-1-benzimidazolinyl)piperidino]ethyl]benzamide hydrochloride monohydrate, having an m.pt. 213°-5° C. (dec.).

Following essentially the same procedure but substituting methyl 2-hydroxy-5-[1-hydroxy-2-[4-(2-oxo-1-benzimidazolinyl)-1,2,3,6-tetrahydro-1-pyridyl]ethyl]-benzoate hydrochloride for the methyl 2-hydroxy-5-[1-hydroxy-2-[4-(2-oxo-1-benzimidazolinyl)piperidino]ethyl]benzoate hydrochloride above results in the formation of 2-hydroxy-5-[1-hydroxy-2-[4-(2-oxo-1-benzimidazolinyl)-1,2,3,6-tetrahydro-1-pyridyl]ethyl]benzamide hydrochloride.

Following essentially the same procedure as above but substituting gaseous methylamine for the gaseous ammonia above, results in the preparation of 2-hydroxy-5-[1-hydroxy-2-[4-(2-oxo-1-benzimidazolinyl)-piperidino]ethyl]-N-methylbenzamide hydrochloride.

Following essentially the same procedure as above but substituting methyl 5-[1-hydroxy-2-[4-(2-oxo-1-benzimidazolinyl)piperidino]ethyl]-2-methoxybenzoate for the methyl 2-hydroxy-5-[1-hydroxy-2-[4-(2-oxo-1-benzimidazolinyl)piperidino]ethyl]benzoate above results in the formation of methyl 5-[1-hydroxy-2-[4-(2-oxo-1-benzimidazolinyl)piperidino]ethyl]-2-methoxybenzamide hydrochloride.

EXAMPLE 3

2-Hydroxy-5-[1-hydroxy-2-[4-(2-oxo-1-benzimidazolinyl)piperidino]ethyl]-N-ethylbenzamide hydrochloride The compound methyl 2-hydroxy-5-[1-hydroxy-2-[4-(2-oxo-1-benzimidazolinyl)piperidino]ethyl]benzoate hydrochloride (8.6 g) is converted to its free base by treatment with sodium bicarbonate solution and extraction into methylene chloride. The combined extracts are evaporated in vacuo and the residue is dissolved in approximately 700 ml of anhydrous methanol to which a small piece (about 100 mg) of metallic sodium has been added. To this mixture 14.1 g of ethylamine is added and the reaction mixture is stirred at room temperature for approximately 4 days. The reaction is observed via thin layer chromatography and additional sodium methoxide catalyst is added as required. Upon completion of the reaction the solvent is removed in vacuo and one equivalent of methanolic HCl is added to the residue. The desired 2-hydroxy-5-[1-hydroxy-2-[4-(2-oxo-1-benzimidazolinyl)piperidino]ethyl]-N-ethylbenzamide hydrochloride is precipitated by the addition of diethyl ether and recrystallized from an isopropanol-water mixture to yield a product having a m.pt. of 222°–4° C. (dec.).

Following essentially the same procedure but substituting an equivalent amount of neopentylamine and dodecylamine for the ethylamine above, results in the formation of 2-hydroxy-5-[1-hydroxy-2-[4-(2-oxo-1-benzimidazolinyl)piperidino]ethyl]-N-(2,2-dimethylpropylbenzamide hydrochloride and 2-hydroxy-5-[1-hydroxy-2-[4-(2-oxo-1-benzimidazolinyl)piperidino]ethyl]-N-dodecylbenzamide hydrochloride, respectively.

EXAMPLE 4

The following Example is illustrative of the $\alpha$ and $\beta$-adrenergic blocking activity and the direct spasmolytic activity for the compounds of this invention.

$\alpha$-Adrenergic receptor blocking activity is determined in vitro by performing cumulative dose-response experiments in the isolated rabbit aortic strip preparation using norepinephrine as the agonist. The contractile response of the rabbit strip preparation in the presence of logarithmically increasing concentrations of the compounds being tested are expressed as percent of the maximal attainable response. Relative antagonistic potency is expressed as a $pA_2$ value. The $pA_2$ is defined as the negative logarithm of the concentration of the antagonist which produces a doubling of the concentration of agonist required to produce a 50% maximal contraction. The resulting $pA_2$ values for several of the compounds of this invention are shown in Table I below.

$\beta$-Adrenergic receptor blocking activity is determined in vitro by performing cumulative dose-response experiments in the isolated guinea pig atria preparation using isoproterenol as the agonist. The response (increase in rate) of the guinea pig atria preparation in the presence of logarithmically increasing concentrations of the compounds being tested are expressed as percent of the maximal attainable response. Relative antagonistic potency is expressed as a $pA_2$ value, as defined above. The $pA_2$ values for various compounds of this invention are shown below in Table I.

Direct spasmolytic activity is determined in vitro by performing cumulative dose response experiments in the isolated guinea pig ileum preparation using barium chloride as the agonist. The contractile response of the guinea pig ileum preparation in the presence of logarithmically increasing concentrations of the compounds being tested are expressed as percent of the maximal attainable response. Relative antagonistic potency is expressed as a $pA_2$ value, as defined above. The $pA_2$ values for various compounds of this invention are shown below in Table I.

Table I

| | Direct Spasmolytic Activity | | |
|---|---|---|---|
| | | $pA_2$ | |
| Compound | $\alpha$ | $\beta$ | $BaCl_2$ |
| 1 | 6.94 | 5.71 | 5.90 |
| 2 | 6.70 | 5.45 | <4.20 |
| 3 | 6.63 | <5.38 | 5.16 |
| phentolamine | 7.78 | <5 | 5.70 |
| propranolol | <5 | 8.89 | 5.75 |

| Compound No. | |
|---|---|
| 1 | methyl 2-hydroxy-5-[1-hydroxy-2-[4-(2-oxo-1-benzimidazolinyl)piperidino]ethyl]benzoate hydrochloride. |
| 2 | 2-hydroxy-5-[1-hydroxy-2-[4-(2-oxo-1-benzimidazolinyl)piperidino]ethyl]benzamide hydrochloride monohydrate. |
| 3 | 2-hydroxy-5-[1-hydroxy-2-[4-(2-oxo-1-benzimidazolinyl)piperidino]ethyl]-N-ethylbenzamide hydrochloride. |

EXAMPLE 5

The following Example illustrates the antihypertensive activity for the compounds of this invention.

Antihypertensive activity is determined in spontaneously hypertensive rats (SHR) of the Okomoto-Aoki strain. Systolic blood pressure of the SHR is measured from the caudal artery by means of an indirect method utilizing a photocell transducer/tail cuff occluder system. Time response relationships are determined for each compound following an oral dose of 50 mg/kg. Data are expressed as mm of Hg decrease from control values. Statistical significance is determined using a 2 tailed "t" test comparing drug treatment response values to those obtained from concurrent vehicle treated animals.

The compound 2-hydroxy-5-[1-hydroxy-2-[4-(2-oxo-1-benzimidazolinyl)piperidino]ethyl]-N-ethylbenzamide hydrochloride lowers blood pressure by 22 and 51 mm Hg after 1 and 4 hours, respectively, upon oral administration.

We claim:

1. A derivative of 2-hydroxy-5-[1-hydroxy-2-[4-(2-oxo-1-benzimidazolinyl)piperidino]ethyl]benzoic acid having the formula

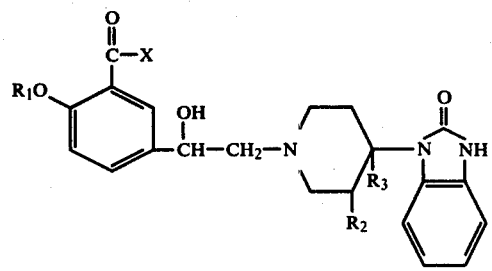

wherein
X is selected from the group consisting of hydroxy, methoxy, ethoxy, amino, dimethylamino and alkylamino in which the alkyl group has from 1 to 12 carbon atoms;
$R_1$ is hydrogen, methyl or ethyl;

$R_2$ and $R_3$ are hydrogen or when taken together form a double bond;

and the pharmaceutically acceptable acid addition salts thereof.

2. A compound according to claim 1 wherein X is amino, dimethylamino or alkylamino in which the alkyl group has from 1 to 12 carbon atoms; and $R_1$, $R_2$ and $R_3$ are hydrogen.

3. A compound according to claim 1 wherein X is methoxy or ethoxy; and $R_1$, $R_2$ and $R_3$ are hydrogen.

4. A compound of claim 1 which is methyl 2-hydroxy-5-[2-[4-(2-oxo-1-benzimidazolinyl)-1-piperidinyl]-1-hydroxyethyl]benzoate and its pharmaceutically acceptable acid addition salts.

5. A compound of claim 1 which is 2-hydroxy-5-[2-[4-(2-oxo-1-benzimidazolinyl)-1-piperidinyl]-1-hydroxyethyl]benzamide and its pharmaceutically acceptable acid addition salts.

6. A compound of claim 1 which is 2-hydroxy-5-[2-[4-(2-oxo-1-benzimidazolinyl)-1-piperidinyl]-1-hydroxyethyl]-N-ethylbenzamide and its pharmaceutically acceptable acid addition salts.

* * * * *